United States Patent [19]

Tsuei

[11] Patent Number: 4,795,636
[45] Date of Patent: Jan. 3, 1989

[54] METHOD FOR TREATING GENITAL AND ORAL HERPES

[76] Inventor: Julia J. Tsuei, 935 Kaluanui, Honolulu, Hi. 96825

[21] Appl. No.: 799,956

[22] Filed: Nov. 20, 1985

[51] Int. Cl.$^4$ ............................................... A61K 35/78
[52] U.S. Cl. .................................. 424/195.1; 514/934
[58] Field of Search ....................... 424/195.1; 514/934

[56] References Cited

U.S. PATENT DOCUMENTS 2,618,561 11/1952 Spinka et al. ..................... 424/195.1
2,642,374 6/1953 Seebeck ............................. 424/195.1

FOREIGN PATENT DOCUMENTS 153881 4/1985 European Pat. Off. .
842404 7/1960 United Kingdom .
1157717 7/1969 United Kingdom .

OTHER PUBLICATIONS

Bulatov, et al., 28 Sovietskaia Meditsina 86 (Dec. 1965) (Russian version with English summary enclosed).
Esanu, "Recent Advances in the Chemotherapy of Herpes Virus Infections," 32 Virologie 57 (Jan.-Mar. 1981).
Sekeley, et al., "Anti-Viral Activity of Azathymidine and Uracil Methyl Sulphone", 211 Nature 1260 (1966).
Tsai, et al., "Antiviral Properties of Garlic: *In Vitro* Effects on Influenza B, Herpes Simplex and Coxsackie Viruses", 1985 Planta Medica No. 5,357 (Oct. 1985).

*Primary Examiner*—John Rollins
*Attorney, Agent, or Firm*—Lyon & Lyon

[57] ABSTRACT

A method for treating herpes simplex virus is disclosed in which a sufferer is treated with garlic or a garlic preparation such as a health food mixture containing such garlic extract or the active ingredient of the garlic. The treatment can be done either orally or topically, and the treatment delays and minimizes the symptoms of the virus, as well as increasing the period of time between recurrences of viral shedding.

10 Claims, 3 Drawing Sheets

METHOD FOR TREATING GENITAL AND ORAL HERPES

FIELD OF THE INVENTION

The present invention relates to a method of treating genital or oral herpes virus by topical or oral administration of a natural composition in order to reduce the extent and recurrence of outbreaks of the virus.

BACKGROUND OF THE INVENTION

Genital infection due to Herpes Simplex Virus (HSV2) is one of the most common venereal diseases in the United States today. Genital herpes infections have reached epidemic proportions in the U.S. during the last decade, and other areas of the world, such as Asia, have reported a similar situation. It is estimated that 5 million people suffer from genital herpes infection in the U.S., and that 200,000 to 500,000 uninfected individuals will contract it each year.

The epidemic of genital herpes differs from other common venereal diseases in that the virus currently has no cure. It is a self-limiting disease in itself, but continued recurrences plague the individual throughout his or her lifetime, creating psychological and sexual problems. During the course of primary infection, the virus travels via sensory nerves to the dorsal root ganglia where it can establish a latent state, and from this latent state the virus can reactivate at any time.

Furthermore, a pregnant woman with an active infection at the time of delivery can transmit the virus to her newborn child. About 1,000 children are born each year to herpes infected mothers. Of those delivered vaginally in the presence of viral shedding, 40% become infected. Of those infected, nearly 50% die. The rest will be compromised with infections of the eyes, skin, and viscera, and 25% will be mentally retarded. In addition, there has been a strong association between HSV2 and cervical cancer. Although researchers consider that genital herpes is more responsible for the above conditions, recent reports indicate that oral herpes (HSV1) may affect individuals in a similar manner. See, e.g., Viral Infections of Humans, edited by Alfred S. Evans, Chapter 13 (1984).

Most genital herpes infections are the result of direct contact with infected mucosal or skin lesions. The attack rate from sexual contact is approximately 30 to 50 percent. Clinical manifestations are normally preceded by an incubation period that averages four to seven days. In primary infections, the patients usually experience fever, malaise, and local inguinal adenopathy. Males may experience urethritis while females may suffer vulvitis, vaginitis, and cervicitis. Itching, tension, and pain may precede the development of vesicles that rapidly appear on an erythematous base that contains clear exudate. In most instances, the lesions are localized and consist of groups of three to ten vesicles that crust and heal without scarring after 10 to 14 days. Fifty-three percent of patients with genital herpes experience one or more recurrences per month, 33% have a recurrence every two to four months, and 14% have recurrences less than once every four months. Twenty-four percent of adult patients with oral herpes have a recurrence one or more times per month, 58% once every two to four months, and 18% less than once every four months. (See Medical Clinics of North America, September 1983).

Over the years, various substances have been postulated as medications for the various kinds of herpes. Examples include a mixture of vitamin C and vitamin P for herpes simplex labialis (U.S. Pat. No. 4,049,798), a mixture of kelp and a carrier (U.S. Pat. No. 4,117,120), extract of mountain ash berries (U.S. Pat. No. 4,132,782), a water soluble extract from marine red alga (U.S. Pat. No. 4,162,308), an antiviral lignosulfate (U.S. Pat. No. 4,185,097), 1-amino-2, 4-ethanobicyclo[3, 3, 1]nonane or salts thereof (U.S. Pat. No. 4,230,725), and a suspension of boric acid, tannic acid, and salicylic acid, preferably in an ethanol solvent/carrier (U.S. Pat. No. 4,285,934). As of now, however, there has been no curative drug found to treat genital herpes and there is only one licensed drug usable for its treatment. Acyclovir has been approved in both atopical and oral form by the Food and Drug Administration and is now available with a prescription. When applied topically in initial or primary genital herpes in males and females, the drug has been observed to reduce the duration of viral shedding, hasten the resolution of lesions, and decrease other symptoms. In the form of oral administration, when one Acyclovir capsule (200 mg) was given five times a day for five days, the duration of viral activity, the time of crusting and healing of lesions, and the formation of new lesions were reduced. When taken daily for up to six months (the manufacturer states that it is not advisable to take it for more than six months), it can prevent or reduce recurrences during the period of therapy, but not thereafter. The most common problem in herpes sufferers is still the frequency of recurring genital herpes, which may be disabling to the patients.

In addition, as with any drug, two major factors must be taken into account: (1) emergence of drug-resistant mutant strains of genital herpes; and (2) the cost of the drug. Acyclovir, which is an analog of nucleoside gunosine, is phosphorylated by herpes viruses that induce virus-coded thymidine kinase. It has been shown that thymidine kinase negative mutant strains of herpes viruses exist in nature, and treatment with acyclovir can induce this resistance by selection or mutation. See, e.g., Darby, 50(3) JOURNAL OF VIROLOGY 838 (1984). Thymidine kinase negative mutants of herpes virus strains are shown to be more virulent. A secondary action of acyclovir is inhibition of herpes-induced viral DNA polymerase, but it has been noted tha this mechanism of inhibition by acyclovir is not operative on some strains of herpes viruses.

The cost of the drug is also important. A 15 g tube of acyclovir ointment currently costs $16 to $24. A 200 mg Acyclovir capsule currently costs 70 cents, a five day regimen $17.50, and a six month regimen $630. Recurrent genital herpes infection will require frequent treatments with acyclovir and therefore any relief from symptoms can be quite expensive. In addition, acyclovir is a synthetic analog of nucleoside gunosine. The long-term effects of this synthetic drug are unknown so that in the long run the continued use of the drug may create cost problems as well as reducing its effectiveness.

After extended use, acyclovir is considered toxic so there must remain periods when the drug is not used to avoid a toxicity overload. During these periods, all of the normal problems and symptoms of genital herpes return.

Accordingly, there exists a need for a method of treating genital and oral herpes simplex virus that is natural, non-toxic, reduces the duration of viral shedding, decreases other symptoms, and increases the time between, or eliminates, recurrences.

SUMMARY OF THE INVENTION

The present invention relates to a method of treating genital or oral herpes by topical or oral administration of garlic or a preparation thereof, or the active ingredient or ingredients therein, in order to reduce the extent and the recurrence of outbreaks of the herpes simplex virus.

DETAILED DESCRIPTION OF THE INVENTION

Figure 1:
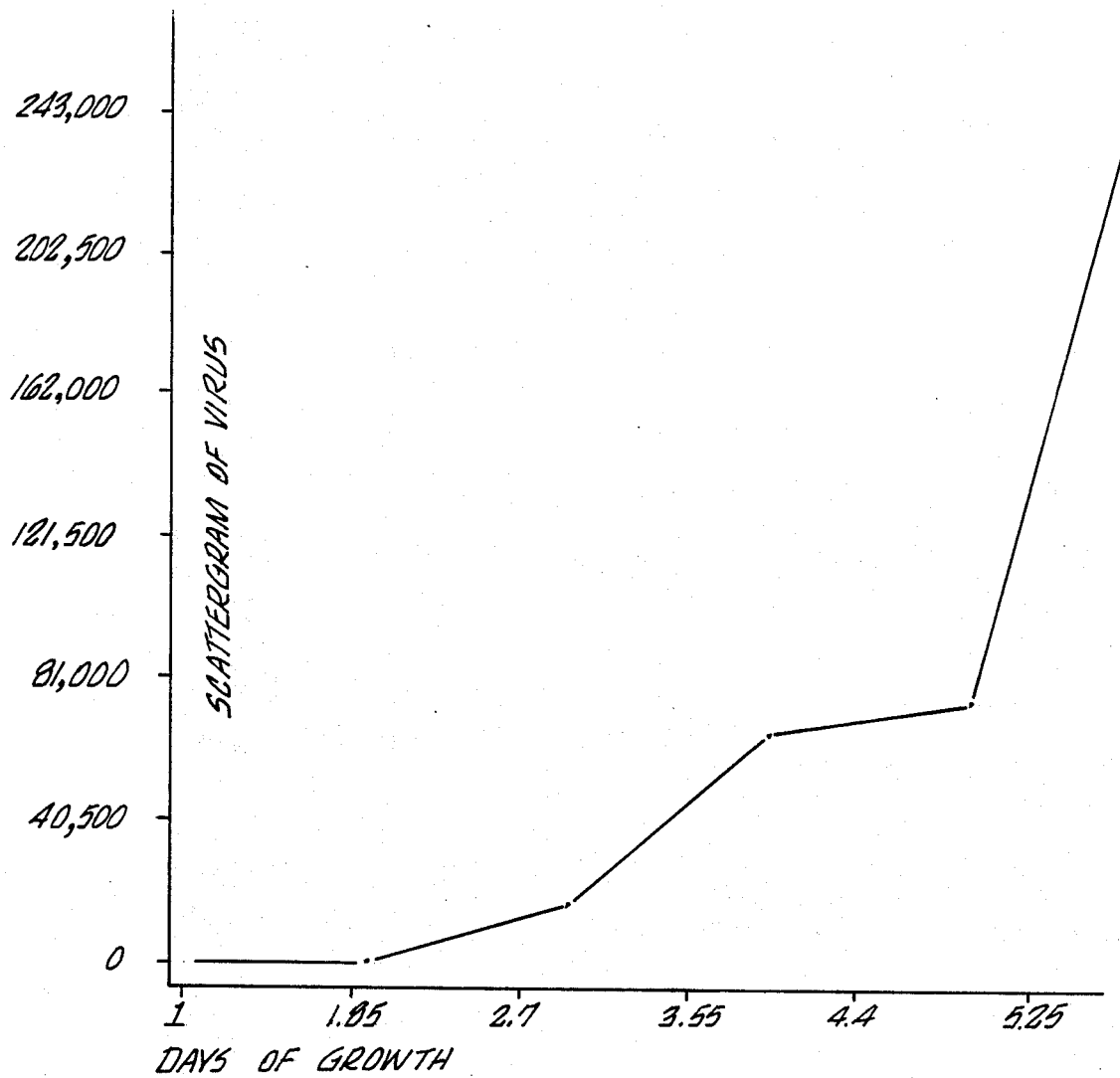
FIG. 1 shows a typical HSV2 growth pattern in cell culture.

It has been found that the oral or topical application of garlic or a preparation thereof acts to markedly inhibit the outbreak of genital herpes virus.

While initial testing was performed using kyolic, a preparation made by low temperature, high pressure extraction of raw garlic with the addition of a minimum amount of vitamins B1 and B12, it has been shown that the active ingredient is one of the components of garlic. Kyolic, manufactured by the Wakanuga Company of Japan, is used as a health food supplement and is taken regularly by hundreds of individuals in many parts of the world.

Preliminary in vitro studies in tissue culture of Herpes Simplex Virus 2 (HSV2) strain isolated from a human patient suffering from genital herpes showed that the addition of kyolic after absorption of virus into the cells caused a definite decrease in the production of HSV2 for the next three days at various concentrations of kyolic.

Flow 2000, a human diploid fibroblastic cell line, was used. Flow 2000 cells are derived from a human fetal lung. The cells have a fibroblast appearance in cell culture and are susceptible to a variety of viruses. Herpes causes a distinct cytopathic effect (CPE) in Flow 2000. (Cytopathic effect refers to a change in the normal appearance of a cell after it has been infected by a virus. The changes can range from no apparent change to complete destruction of the cell. Some virus CPE is visually unique in some cell lines.) Flow 2000 is used because it is easy to maintain and because of its sensitivity to herpes virus. In addition, since it is a human cell line, it is very appropriate for antiviral study.

Flow 2000 monolayers in 25 square centimeter flasks were infected with an isolate of genital herpes virus (HSV-2) from a patient (strain 28382) at a multiplicity of infection (MOI) of about 0.1. (MOI is the ratio of virus to cells that the virus is infecting e.g., 500 viruses/1000 cells equals an MOI of 0.5.) Virus was absorbed onto cell monolayers at 37° C. for one hour and then dilutions of kyolic were added to the culture media. Alloquots of cell culture supernatents were taken and assayed in BHK-21 (Baby Hamster Kidney—Clone 21) cells for the growth of virus. These cells are excellent for assay of herpes virus. Growth is measured by counting the number of plaques or infectious centers produced in the BHK-21 cells. The plaque forming units, or PFU, is the number of infections units per ml. of the culture fluid assayed.

TABLE I
GROWTH OF HSV2* IN CULTURE IN THE PRESENCE OF DIFFERENT CONCENTRATIONS OF KYOLIC AS COMPARED TO CONTROL WITH NO DRUG TREATMENT

| Drug Conc. | Day 1 | Day 2 | Day 3 |
|---|---|---|---|
| Control (no drug) | 10 | 100 | 2000 |
| **KYOLIC | | | |
| 1:20 | 0 | 0 | 4 |
| 1:40 | 0 | 18 | 480 |
| 1:80 | 0 | 30 | 300 |
| 1:160 | 8 | 32 | 1800 |

*Plaque-forming units per ml.
**Final concentration of the drug as diluted with standard Hank's Balanced Salt Solution.

Similar experiments were carried out using a purified garlic extract. The pure garlic extract was obtained by subjecting standard garlic powder to ethanol extraction. The powdered garlic was dissolved in a 30% ethanol solution in an environment of 4°–10° C. (standard for dealing with natural ingredients). A magnetic stirrer agitated the solution for 24 hours and the residue was then spun down in a Beckman J21 centrifuge. The supernatant was evaporated in a flash evaporator and then lyophilized to dryness. Certainly, however, other methods of purifying garlic could be used the scope of this invention. A comparison of regression slopes on the antiviral effect of garlic versus kyolic indicates that pure garlic extract is at least 250 times as effective as kyolic. Table II shows the effect of low and high concentrations of kyolic and garlic on virus titer as compared to an untreated infection.

TABLE II
PERCENT REDUCTION OF VIRUS PRODUCTION IN PRESENCE OF DRUG COMPARED TO CONTROL

| COMPOUND | DAY 1 | DAY 2 | DAY 3 | DAY 4 | DAY 5 | DAY 6 |
|---|---|---|---|---|---|---|
| Kyolic 1:160* | 17% | 50% | 10% | <10% | <10% | <10% |
| Kyolic 1:40* | 100% | 100% | 99.95% | 80% | <10% | <10% |
| Garlic 1:160* | 100% | 100% | 100% | 99.99% | 99.99% | 83.05% |
| Garlic 1:40* | 100% | 100% | 100% | 99.99% | 99.99% | 99.99% |

*As diluted with standard Hank's Balanced Salt Solution.

Figure 2:
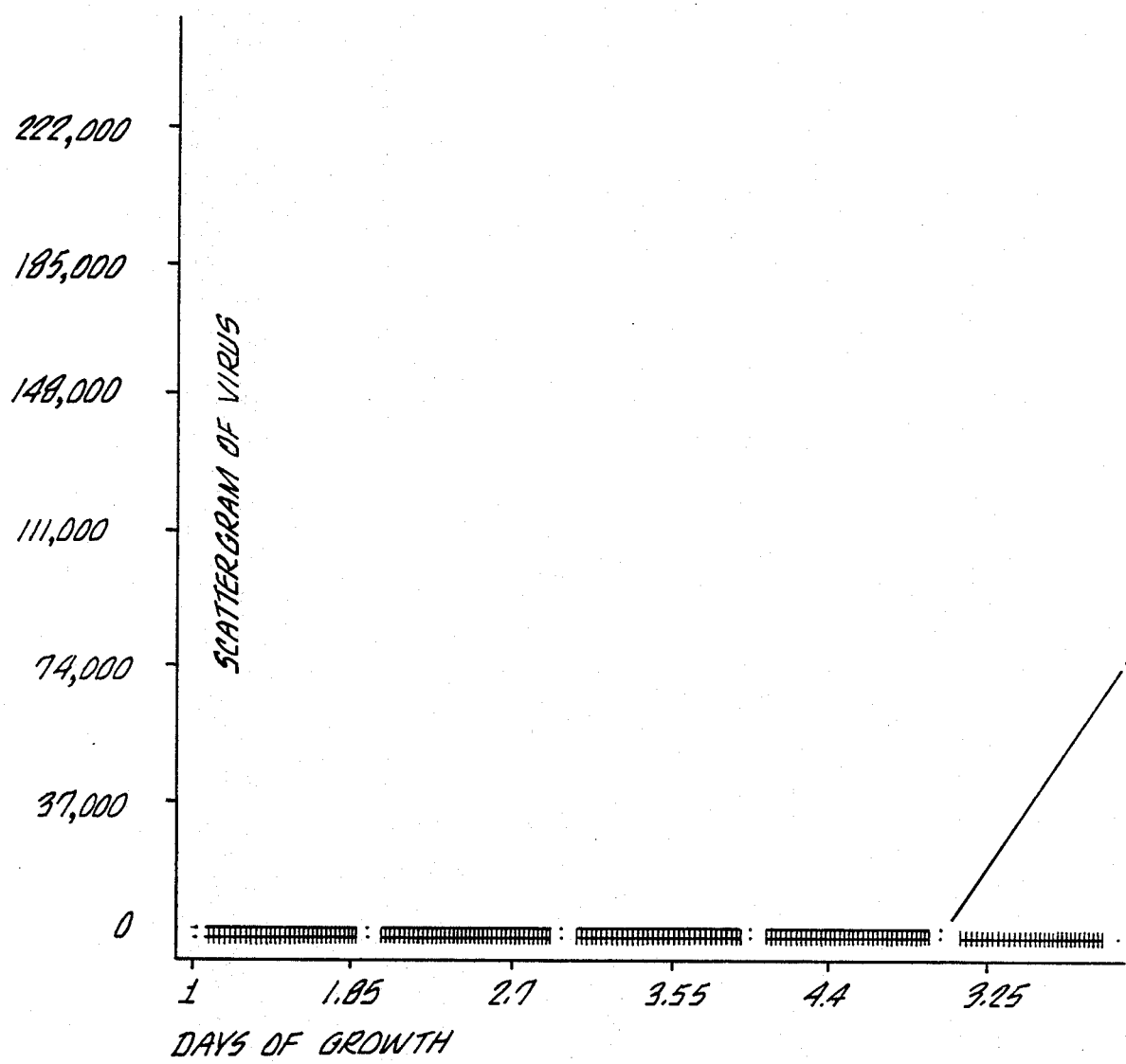
FIG. 2 illustrates the HSV2 growth pattern when cell cultures are treated with pure garlic extract.

The effect of pure garlic in reducing the concentration of virus is dramatic. FIG. 1 shows a typical HSV2 growth pattern over a period of several days. In contrast, FIG. 2 shows the HSV2 growth pattern when the cell cultures are treated with low and high concentrations of garlic. The marked difference can readily be seen.

Further studies were performed using experimental animals. Genital herpes infection has been successfully established and extensively studied in female guinea pigs following intravaginal inoculation. Because of the herpetic lesions on the external genitalia of guinea pigs and intermittently recurring infection in this animal species and because cytologic smears taken from genitally herpes infected guinea pigs show similarities to those observed in Pap smears taken from women with herpes genital infection, guinea pigs are the most commonly used animal models in the study of the pathogenesis of herpes genital infection.

Preliminary studies on the toxicity of kyolic showed no toxicity in guinea pigs over a period of two weeks when administered orally and/or topically. Thereafter, nine guinea pigs were infected with HSV2. Eight of the guinea pigs were treated with kyolic—four as soon as the infection was induced and four after vaginal lesions appeared. One guinea pig was not treated and served as a control. Table III illustrates the results of this procedure.

TABLE III

RESULTS OF TREATMENT WITH KYOLIC** ON EXPERIMENTAL INTRAVAGINAL INFECTION OF GUINEA PIGS WITH HSV2

| Animal No. | Treatment | Virus shedding from the lesion | | | |
|---|---|---|---|---|---|
| | | Day 3 | Day 4 | Day 8 | Day 10 |
| K1 | Infect & Treat | + | — | — | — |
| K2 | Infect & Treat | + | — | — | — |
| K3 | Infect & Treat | + | — | — | — |
| K4 | Infect & Treat | ++++ | ++++ | + | — |
| K5 | Treat when Lesions appear | + | ++ | + | — |
| K6 | Treat when Lesions appear | + | ++++ | + | — |
| K7 | Treat when Lesions appear | + | ++ | + | — |
| K8 | Treat when Lesions appear | + | ++ | + | — |
| Control | No Treatment | ++++ | ++++ | ++++ | — |

++++ = High concentration of virus
++ = Intermediate concentration of virus
+ = Low concentration of virus
— = Negative for virus
**Systemic (oral) and topical administration of kyolic Three out of four guinea pigs (K1, K2, and K3) treated immediately showed substantially less virus on day 3 and no virus on days 4, 8 and 10. The fourth guinea pig immediately treated (K4) showed a marked reduction of virus on day 8 compared to the control animal. The four guinea pigs (K5–K8) treated after the appearance of lesions, while showing a virus shedding pattern peaking around day 4, all showed generally and substantially reduced concentration of virus throughout the experimental cycle when compared to the control animal. The shedding cycle appeared to have run its course in the control animal by day 10. Thus, it appears that kyolic can arrest the growth of virus in lesions after they appear, reduce the number of lesions, and enhance the rapid clearance of the virus and the lesions.

Figure 3:
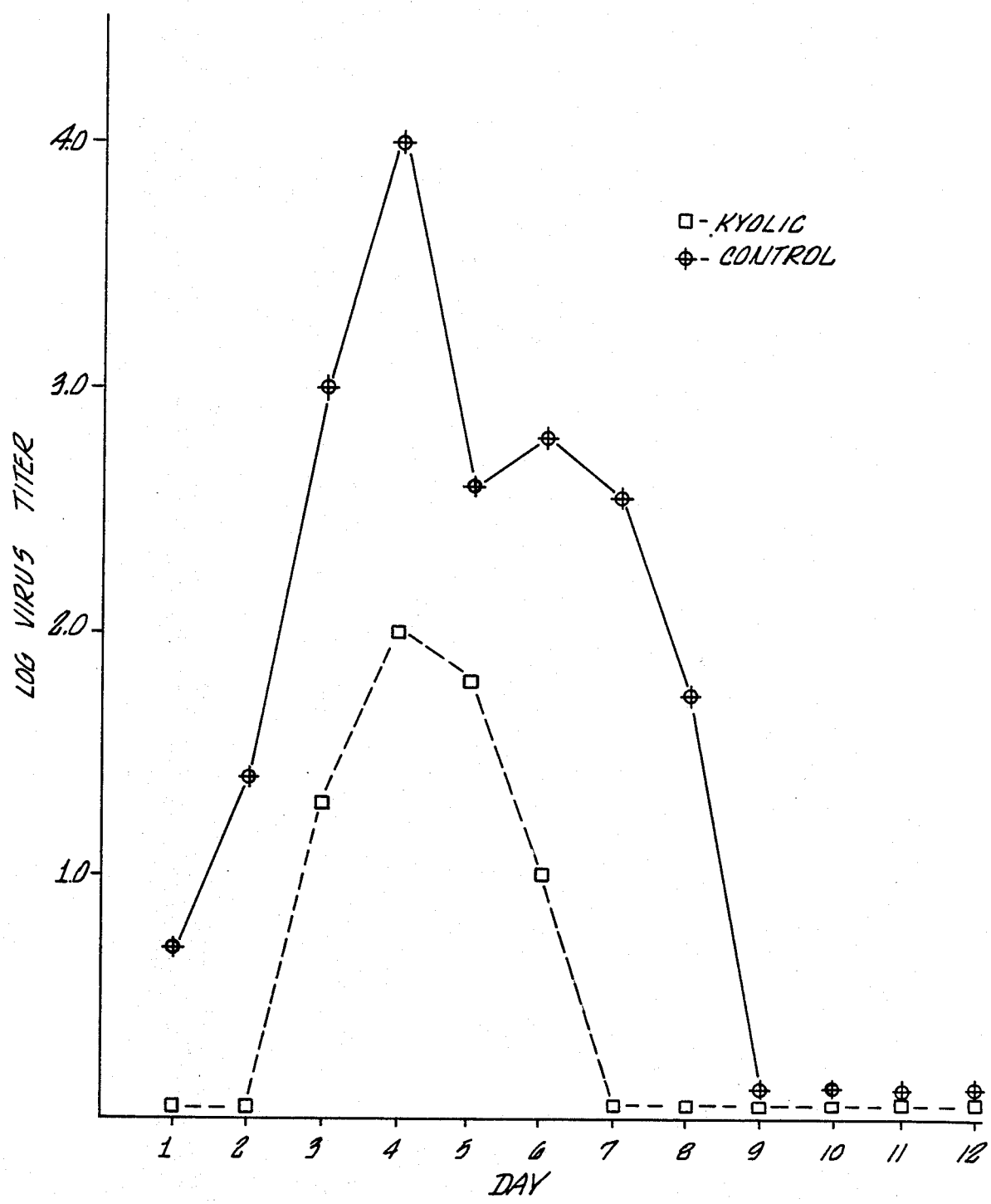
FIG. 3 illustrates the results of treating infected guinea pigs with a garlic preparation, kyolic.

Further support was found in another in vivo experiment. Seven female guinea pigs were infected intravaginally with 0.1 ml, 1,000 PFU HSV2 strain 28382. Five guinea pigs were treated with kyolic by oral administration of 0.2 ml and by topical administration and the two others received no treatment. Vaginal swabs were collected four times daily from each of the animals for a period of twelve days and virus content was determined by plaque assay using tissue culture. FIG. 3 shows the composite results of this experiment using the virus content of the vaginal swabs. The top curve represents the control group results. Peak shedding of herpes virus amongst the control group occurred on day 4 and virus was detected in the lesions up until day 9. By contrast, the bottom curve illustrates the virus shedding pattern in the kyolic treated animals. Virus shedding was delayed by one day while peak shedding occurred on day 4, the same day as with the control group. The amount of virus shedding, however, was only 1% of that in the control group (100 infection units versus 10,000 infection units). In addition, the duration of the shedding period was reduced so that it ended on day 7. Thus the total shedding period for the treated guinea pigs was only six days as compared to nine days for the control guinea pigs. It was also observed that the size of the lesions was markedly reduced in the treated animals.

While in vivo ttudies involving humans have not been completed at the present time, preliminary observation in a few patients confirms the usefulness of kyolic and garlic as a treatment for herpes sufferers. For example, Case L.S., a 44 year old white female, during her first visit, complained that for one year, she had suffered from herpes lesions on her labia minora and buttocks. These lesions broke out approximately every month, either before mensis or when she was under stress. Laboratory culture proved that she had Herpes Type II virus. She was treated with 16 ml. of kyolic per day for one week and 8 ml. per day thereafter. Kyolic was also painted on the lesions externally when there was an outbreak. During the first three months of treatment, new lesions sometimes broke out in less than one month intervals, but after three months the interval of recurrence prolonged to a month and a half, and after six months the interval prolonged to three and a half months. Patient discontinued kyolic treatment after one year and three months and has remained symptom free for at least six months thereafter without treatment.

Efforts have been made to isolate the active ingredient contained in kyolic and garlic using fractionation. Powdered garlic extract was extracted with 30% ethanol in a cold room using a magnetic stirrer for 24 hours and the residue was then spun down in a Beckman J21 centrifuge at 20,000 r.p.m. for 30 minutes. The supernatant was evaporated in a flash evaporator and then lyophilized to dryness. The dried extract was dissolved in distilled water and the proper amount was put into a Sephadex G15 column taat had been equilibrated with 0.03 M ammonium acetate. The G15 column has an exclusion limit of 1,500 M.W. The extract was then eluted with ammonium acetate and fractions were collected according to the absorption peak at 254 nm.

Six fractions were isolated and results of the biological assay by tissue cllture revealed that Fraction II was active. More studies were performed to further isolate the active component. Fraction II was subfractioned by SEP-PAK (Waters Associates, Milford, MA), which are $C_{18}$ cartridges that eliminate high polarity compounds with a polar solvent and sequentially elute the remaining compounds with less polar solvents. Again six subfractions were collected and it was found that the polar subfraction was active according to the biological assay.

The polar subfraction of Fraction II was then put in an HPLC (High Pressure Liquid Chromatography) machine. On the basis of polarity, the polar subfraction was separated and yielded 10 fractions. The biological assay revealed that three of these 10 fractions were active. Using a standard Lowry Protein measurement procedure with Folin-Ciocalteu phenol reagent, positive results were obtained indicating a high probability that the active ingredient is a protein. At the present time, additional studies need to be conducted to investigate the physical properties, molecular structure and mode of action of this active anti-viral component of garlic. However, it has been determined that the active component is water soluble, probably a protein, contains charged compounds, and has a molecular weight below 1500.

Thus, it is apparent that a subfraction of garlic is effective in treating herpes virus. While it may be more appropriate to use the subfraction by itself, it is also apparent that garlic or garlic in combination with other compounds can be effective. Active ingredients obtained from both kyolic and pure garlic showed the same effectiveness regardless of the origin or age of the starting material. The use of garlic or a garlic subfraction will be substantially cheaper while being more effective and less toxic than the currently available acyclovir.

While the method of this invention has been particularly shown and described with reference to preferred embodiments, many ther modifications and uses of this method will be apparent to those skilled in the art upon reading this specification and examining the accompanying Figures. In particular, while some of the experiments were carried out using both topical and oral applications, either of those metoods could be used without the other and it is possible that an injection method would also be appropriate. The invention therefore is not intended to be limited other than by the lawful scope of the following claims.

What is claimed is:

1. A method of treating viral infections caused by Herpes Simplex virus that comprises the step of administering to a subject infected with said virus garlic or a garlic preparation in an effective amount for controlling said virus and reducing the extent of the infection caused by said virus.

2. The method of claim 1 wherein said garlic preparation is kyolic administered topically to an infected area.

3. The method of claim 1 wherein said garlic preparation is kyolic administered orally.

4. The method of claim 3 wherein the kyolic is administered in an amount between 4 ml and 20 ml per day.

5. The method of claim 3 wherein the kyolic is administered in an amount between 16 and 20 ml per day for one week and then in an amount between 8 and 10 ml per day for a second week and then in an amount between 2 and 6 ml per week thereafter.

6. A method of treating viral infections caused by Herpes Simplex virus that comprises the step of administering to a subject infected with said a virus pure garlic extract in an effective amount for controlling said virus and reducing the extent of the infection caused by said virus.

7. The method of claim 6 wherein the pure garlic extract is administered topically to an infected area.

8. The method of claim 6 wherein the pure garlic extract is administered orally.

9. The method of claim 8 wherein the pure garlic extract is administered in an amount between 1 ml and 20 ml per day.

10. The method of claim 8 wherein the pure garlic extract is administered in an amount between 4 and 20 ml per day for one week and then in an amount between 2 and 10 ml per day for a second week and then in an amount between 0.5 and 6 ml per week thereafter.

* * * * *